United States Patent [19]

Miya et al.

[11] Patent Number: 4,515,943

[45] Date of Patent: May 7, 1985

[54] CRYSTAL OF BETA-NICOTINAMIDE-ADENINE-DINUCLEOTIDE AND PROCESS FOR PREPARING THE SAME

[75] Inventors: Toyofumi Miya; Yukiharu Kobayashi; Masao Yano, all of Saiki, Japan

[73] Assignee: Kohjin Co., Ltd., Tokyo, Japan

[21] Appl. No.: 486,935

[22] Filed: Apr. 19, 1983

Related U.S. Application Data

[63] Continuation of Ser. No. 309,467, Oct. 7, 1981, abandoned.

[30] Foreign Application Priority Data

Oct. 12, 1980 [JP] Japan .................. 55-143012

[51] Int. Cl.$^3$ .................. C07H 19/20; C07H 21/02
[52] U.S. Cl. .................. 536/27; 536/28; 536/29
[58] Field of Search .................. 536/26, 27, 28, 29

[56] References Cited

U.S. PATENT DOCUMENTS

| | | | |
|---|---|---|---|
| 3,435,026 | 3/1969 | Samejima et al. | 536/26 |
| 3,700,654 | 10/1972 | Brusca | 536/27 |
| 4,148,994 | 4/1979 | Muhlegger et al. | 536/27 |
| 4,151,349 | 4/1979 | Traeger et al. | 536/27 |

OTHER PUBLICATIONS

Winer; A., J. Biol. Chem., vol. 239, pp. 3598–3600, 1964.

*Primary Examiner*—Blondel Hazel
*Attorney, Agent, or Firm*—Armstrong, Nikaido, Marmelstein & Kubovcik

[57] ABSTRACT

Novel highly pure and stable crystals of $\beta$-nicotinamide-adenine-dinucleotide tetrahydrate (NAD) which is triclinic system and has a space group of $P\bar{1}$ or P1 and lattice constants: a=8.861 Å, b=11.181 Å, c=8.630 Å, $\alpha=90.82°$, $\beta=103.40°$ and $\gamma=109.71°$. The crystalline NAD is prepared by cooling a 20 to 60 w/v % aqueous solution of amorphous NAD, which has preferably been treated with a porous weakly basic anion exchange resin to remove impurities, at a temperature of 0° to 20° C. When the crystalline NAD is added to the aqueous solution as seeds, the desired high pure crystalline NAD is prepared without conducting the treatment of amorphous NAD with the porous weakly basic anion exchange resin. A high pure amorphous NAD is obtained from the crystalline NAD by dissolving the crystalline NAD in water and subjecting the aqueous solution to freeze drying or precipitation with a solvent.

5 Claims, 6 Drawing Figures

RETENTION TIME (min.)

RETENTION TIME (min.)

CRYSTAL OF BETA-NICOTINAMIDE-ADENINE-DINUCLEOTIDE AND PROCESS FOR PREPARING THE SAME

This is a continuation of application Ser. No. 309,467, filed Oct. 7, 1981, now abandoned.

BACKGROUND OF THE INVENTION

The present invention relates to crystals of β-nicotinamide-adenine-dinucleotide of free acid type and a process for preparing the crystals.

β-Nicotinamide-adenine-dinucleotide (hereinafter referred to as "NAD") is present as a coenzyme for various oxidoreductases in almost all of the tissues of living bodies, and has a very important role in energy metabolism, biosynthesis, etc. in a living body. Therefore, in recent years, the demand for NAD has increased not only as reagents for research on biochemistry and physiology, but also as chemicals indispensable to clinical diagnosis as a factor of measurement in enzymatic analysis upon measuring enzyme activity and concentration of a substrate.

Hitherto, NAD has been obtained in solid form by isolating NAD from yeast extract or a cultured broth of a microorganism by various methods of the isolation such as ion exchange chromatography and subjecting the obtained solution of NAD to a method such as freeze drying or precipitaion with an organic solvent followed by separation and drying of the precipitate. The thus obtained solid NAD is amorphous, and is very hygroscopic and deliquesces in air. In many cases, such an amorphous NAD still contains a trace amount of impurities. Also, the amorphous NAD is unstable, and lowering of the purity due to thermal decomposition during storage and transportation is unavoidable. It is known that a competitive inhibitor of an enzyme is present in the thermal decomposition fragments and a trace amount of other impurities. Therefore, it is well known that the use of such a NAD of low purity in the enzymatic analysis gives only results having a large error, for instance, from Dalziel, J. Biol. Chem., Vol. 238, 1538(1963).

Crystallization of NAD of free acid type has been reported by A. D. Winer in J. Biol. Chem., Vol. 239, PC3598(1964). However, this process uses a large amount of a solvent and moreover requires a very low temperature, i.e. $-15°$ C. The standard parameters for this process are indefinite and there is no reproducibility. Also, the disclosed crystals are crystals of NAD trihydrate which are long thin needles or flat prisms, and it is reported that the crystalline NAD changes into the amorphous form by the change in surrounding humidity and the stability is bad. Further, the process has the disadvantage that the purified product obtained by the use of a solvent contains a slight amount of the unseparable solvent. Also, the use of a large amount of a solvent is not economical, and the process has no practical importance as an industrial process.

Crystals of a metal salt of NAD such as the lithium salt are also known. However, when NAD free acid is required, the metal salt must be treated again with an ion exchange resin, and accordingly the purification of amorphous NAD by this process is disadvantageous in increase of the process steps.

It is an object of the present invention to provide novel crystals of NAD of free acid type.

A further object of the invention is to provide crystalline NAD having a high purity and a high stability.

A still further object of the invention is to provide amorphous NAD having a high purity.

Another object of the invention is to provide a process for preparing NAD having a high purity in a simple manner in a high yield.

These and other objects of the present invention will become apparent from the description hereinafter.

SUMMARY OF THE INVENTION

In accordance with the present invention, there is provided a crystalline β-nicotinamide-adenine-dinucleotide tetrahydrate which is triclinic system and has a space group of $P\bar{1}$ or $P1$ and lattice constants: $a = 8.861$ Å, $b = 11.181$ Å, $c = 8.630$ Å, $\alpha = 90.82°$, $\beta = 103.40°$ and $\gamma = 109.71°$.

The crystals are prepared by cooling a 20 to 60 w/v % aqueous solution of amorphous NAD at a temperature of 0° to 20° C. to crystallize NAD tetrahydrate. The process is very simple and the NAD crystals having a high purity and an excellent stability are economically obtained in high yields. The crystals of the invention is very useful for providing amorphous NAD having a high purity.

DETAILED DESCRIPTION

Figure 1:
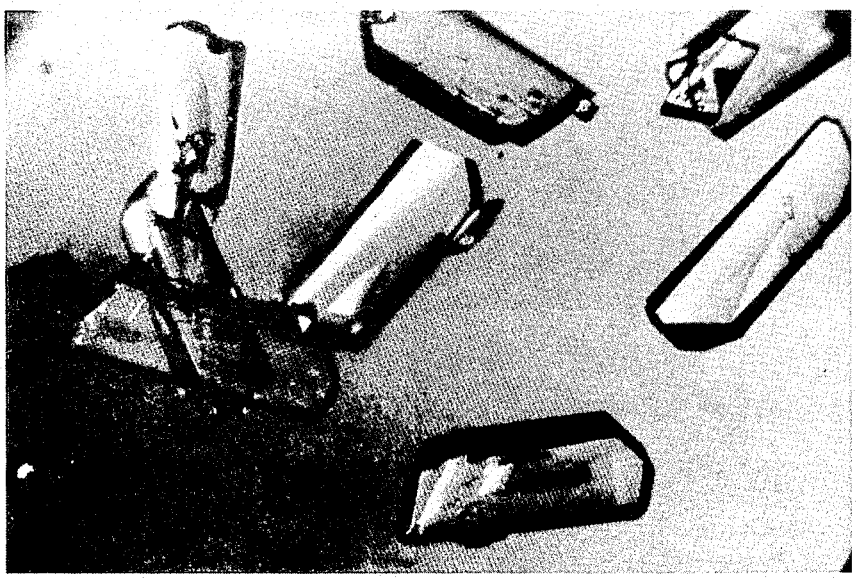
FIG. 1 is a microphotograph of crystalline NAD of the present invention enlarged 400 times.

Amorphous NAD which has been prepared by a generally known method such as precipitation from an aqueous solution of NAD with an organic solvent followed by separation and drying or freeze drying of the aqueous solution, is employed as a starting material for preparing the crystalline NAD of the present invention. In many cases, such as amorphous NAD contains impurities. Impurities can be removed by any known methods. In the present invention, it is desirable that the enzymatic purity of the amorphous NAD is at least 90%, since NAD crystallizes out with ease and also the yield of crystallization increases. Preferably, the amorphous NAD is purified by treating an aqueous solution of amorphous NAD with a porous weakly basic anion exchange resin converted into acetate form, carbonate form, phosphate form, hydrochloride form or OH form (free base form). In a preferable embodiment, the amorphous NAD is purified by passing an aqueous solution of amorphous NAD through a column of a high porous weakly basic anion exchange resin converted into acetate form such as Diaion WA30 (made by Mitsubishi Chemical Industries Ltd.), Amberlite IRA-93 (made by Rohm & Haas Co.), Dowex HWA-1 (made by Dow Chemical Co.), or Duolite A-368PR (made by Diamond Shamrock Corp.). Since NAD is also adsorbed by this anion exchange resin, the anion exchange resin is preferably employed in the smallest amount necessary for removing impurities. NAD crystals of the present invention obtained from an aqueous solution of amorphous NAD purified by this method are very pure and are excellent as seeds for crystallizing NAD.

Upon crystallization, it is necessary for producing the crystals of the invention that the concentration of an aqueous solution of NAD is from 20 to 60 w/v %, preferably 40 to 50 w/v %. When the concentration is less than 20 w/v %, crystallization is hard to occur and the yield is also very low. When the concentration is more than 60 w/v %, the aqueous solution is difficult to handle due to high viscosity. The concentration is adjusted within the above range before or after the purification of NAD. The aqueous solution is cooled at a temperature of 0° to 20° C., preferably 2° to 8° C. for crystallization. Crystallization completes in 1 or 2 days when the aqueous solution is allowed to stand, and in several hours when the aqueous solution is gently stirred to accelerate the growth of crystals.

It is effective to employ, upon crystallization, separately prepared NAD crystals as seeds. In case of conducting the crystallization by employing seeds, the desired crystalline NAD can be obtained by cooling a 20 to 60 w/v % aqueous solution of NAD at a temperature of 0° to 20° C. without subjecting NAD to the purification by means of an ion exchange resin such as the above-mentioned high porous ion exchange resin. Although it is possible to obtain the desired crystals even if the enzymatic purity of the amorphous NAD used is low, preferably the amorphous NAD having an enzymatic purity of not less than 90%, especially not less than 93%, is employed, since the crystallization occurs with ease and also the yield can be increased.

The produced crystals are separated in a usual manner. According to the present invention, the crystals are obtained in a yield of about 90% or more. The NAD crystals of the present invention have the following properties.

Analysis for $C_{21}H_{27}O_{14}N_7P_2.4H_2O$ (M. W.: 735.48): Calcd. (%): C 34.29, H 4.80, N 13.33, P 8.42. Found (%): C 34.57, H 4.73, N 13.28, P 8.40.

Water content by Karl Fischer's method: 9.4% (Theoretical value: 9.8%)

Figure 2:
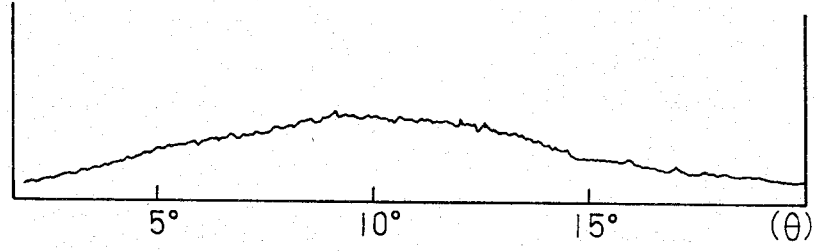
FIG. 2 is an X-ray diffraction spectrum of amorphous NAD.
Figure 3:
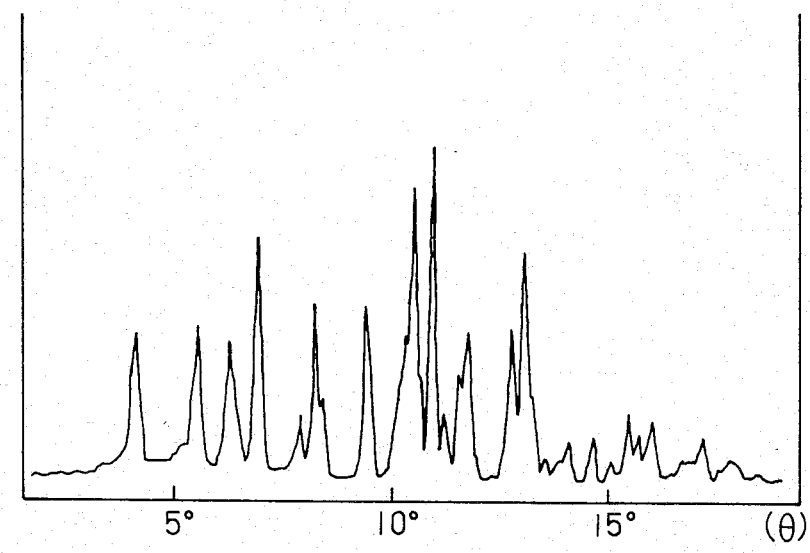
FIG. 3 is an X-ray diffraction spectrum of the crystalline NAD of the present invention.
Figure 4:
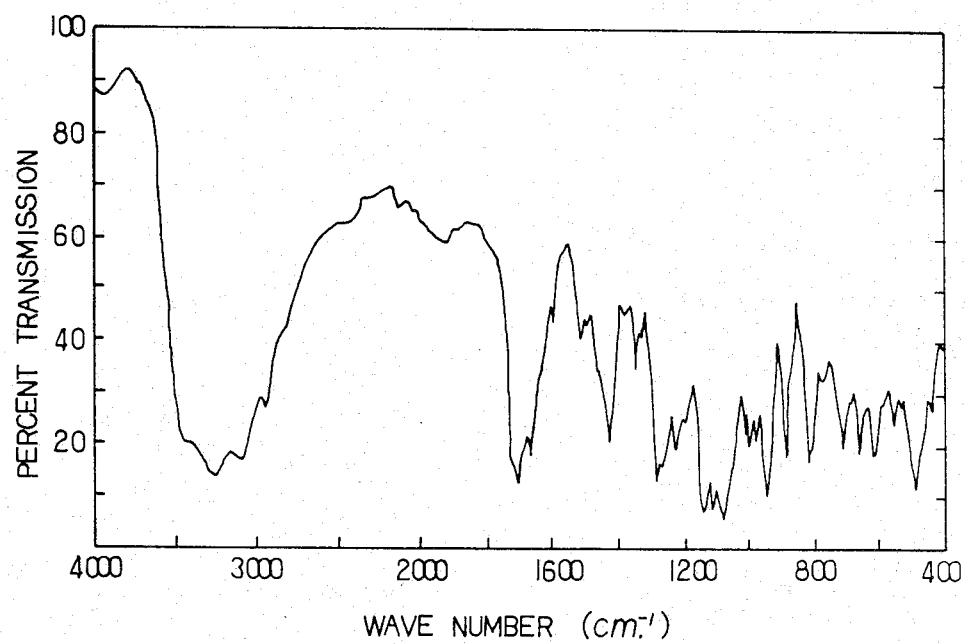
FIG. 4 is an infrared absorption spectrum by KBr tablet method of the crystalline NAD of the present invention.

Crystal system: triclinic system
Space group: P$\bar{1}$ or P1
Lattice constant:
a = 8.861 Å
b = 11.181 Å
c = 8.630 Å
α = 90.82°
β = 103.40°
γ = 109.71°
V = 779.01 Å$^3$ Density: Found ρ = 1.550. Calcd. ρ = 1.567 (calculated as Z = 1). A photograph of the crystals of the present invention observed by a microscope of 100 magnifications is shown in FIG. 1. Also, X-ray diffraction spectrum and infrared spectrum of the crystals of the present invention are shown in FIG. 3 and FIG. 4, respectively. FIG. 2 is an X-ray diffraction spectrum of amorphous NAD.

Figure 5:
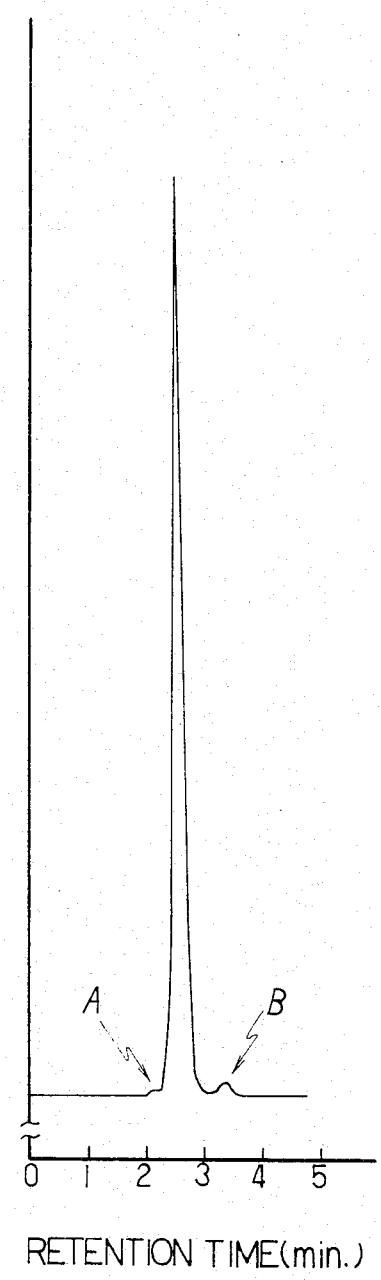
FIG. 5 is a high performance liquid column chromatogram of a purified amorphous NAD powder obtained according to a usual purification method in which methanol is added to an aqueous solution of NAD to precipitate it.
Figure 6:
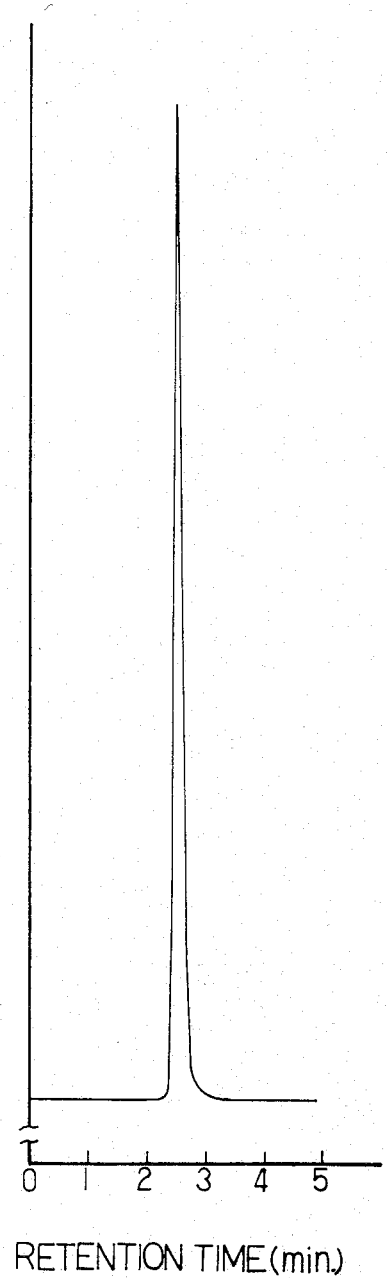
FIG. 6 is a high performance liquid column chromatogram of the crystalline NAD of the present invention.

The thus obtained crystalline NAD of free acid type has no defects of a conventional amorphous NAD. The crystalline NAD of the present invention is crystals having 4 crystal waters, and is stable and is not hygroscopic and has a flowability. It is also excellent in storage stability, and has no odor and a beautiful appearance, and accordingly is of great commercial value. The crystals of the present invention do not lose the crystal framework, even if compulsorily dehydrated, and return easily to the original crystals by giving water. With respect to the stability of the crystals of the invention, the lowering of the enzymatic purity does not occur at all, even if the crystals are maintained, for instance, at 37° C. for 24 days, though amorphous NAD shows lowering of the purity by about 10% under the same condition and lowers its purity with the lapse of time. According to the enzymatic analysis, the crystalline NAD of the present invention is 100% pure as β-NAD, and inclusion of enzyme inhibitors such as LDH (lactate dehydrogenase) inhibitor has not been observed. According to the liquid chromatography, a commercially available β-NAD contains a trace amount of impurities, especially α-NAD and ADP-ribose (adenosine 5-diphosphateribose), but these impurities have not been detected from the crystalline NAD of the present invention. FIG. 5 shows a high performance liquid chromatogram of a commercially available amorphous NAD which has been purified by precipitating NAD with addition of methanol from an aqueous solution of amorphous NAD treated with an ion exchange resin, and FIG. 6 shows a high performance liquid chromatogram of the crystalline NAD of the present invention. In FIG. 5, A is a peak of AMP (adenosine 5-monophosphate) and B is a peak of ADP-ribose. AMP and ADP-ribose are detected in the commercial preparation, but they are not detected in the crystalline NAD of the present invention. The conditions of the high performance liquid chromotography are as follows:

Column: μ-Bondapak NH$_2$ (4 mm. in inner diameter and 30 cm. in length).
Solvent: 0.1M NH$_4$H$_2$PO$_4$ (pH 3.5).
Flow rate: 2.0 ml./min.
Chart speed: 1.0 cm./min.
Detection: UV 254 nm., 0.5 AUFS.
NAD sample concentration: 1.0 mg./ml.

The crystalline NAD of the present invention is very pure, i.e. about 100% pure, and does not contain contaminants which cause errors in enzymatic analysis. Also, it is stable, and upon storage or transportation, there is no necessity of maintaining the temperature low as required for conventional NAD. Further, the process of the present invention has the advantage on industrial production that a purification procedure as conducted in a conventional process in which addition of a large amount of a solvent is repeated is not necessary and the crystals can be obtained from an aqueous solution of NAD without using a solvent.

When a high pure amorphous NAD is desired, it can be easily obtained by dissolving the crystalline NAD of the present invention in water, and then subjecting the resulting aqueous solution to freeze drying or adding the aqueous solution to an alcohol such as methanol to precipitate NAD. For instance, the crystals of the present invention are dissolved in a hot water to prepare a 10 to 50 w/v % aqueous solution of NAD, and the aqueous solution is immediately cooled to room temperature, e.g. 18° to 25° C. in order to avoid the thermal decomposition of NAD. The aqueous solution is then lyophilized, or is poured to an alcohol with agitation to precipitate NAD which is separated and dried. It is apparent from the foregoing description as to crystalline NAD and a process for the preparation thereof that this process for the preparation of amorphous NAD using the crystals of the invention is very superior to a conventional process in that high pure products can be obtained by a simple procedure. Thus, the present invention also provides a process for the purification of amorphous NAD.

The present invention is more specifically described and explained by means of the following Examples.

EXAMPLE 1

A NAD-containing extract obtained from cells of a microorganism was purified by ion exchange chromatography, and the obtained aqueous solution of NAD was added to methanol of 9 times the volume of the aqueous solution to precipitate NAD. The precipitate was filtered, washed with a slight amount of methanol, and dried under reduced pressure to give a powder of purified amorphous NAD. The enzymatic purity of the powder was 92%. The thus obtained amorphous NAD powder was employed as the starting material.

An aqueous solution of 100 g. of the powder dissolved in 200 ml. of water was passed through a column of 1.5 cm. in inner diameter packed with 20 ml. of a high porous weakly basic anion exchange resin converted into acetate form (commercially available under the commercial name "Diaion WA30" made by Mitsubishi Chemical Industries Ltd.) from the top of the column at a space velocity of 1 hr.$^{-1}$ Subsequently, 40 ml. of deionized water was passed through the column, and 220 ml. of the NAD-containing fraction in the eluate was collected.

The fraction was cooled to 5° and allowed to stand at that temperature. After 16 hours, crystals which served as crystal nucleus began to appear on the bottom of a vessel, and subsequently the fraction was gently stirred at 5° C. for 5 hours to produce crystals. The crystals were filtered under suction, washed with a slight amount of water and dried under vacuum to give 90 g. of crystalline NAD tetrahydrate. The enzymatic purity of the crystals was 100% on dry basis.

EXAMPLE 2

A NAD-containing extract obtained from cells of a microorganism was purified by ion exchange chromatography, and the eluate was lyophilized to give purified amorphous NAD, the enzymatic purity of which was 91%.

The procedure of Example 1 was repeated except that an aqueous solution of 500 g. of the above amorphous NAD dissolved in 1 liter of water and Amberlite IRA-93 (made by Rohm & Haas Co.) as an ion exchange resin were employed, to give 455 g. of crystalline NAD tetrahydrate which was 100% enzymatically pure.

EXAMPLE 3

In 200 ml. of water was dissolved 100 g. of an amorphous NAD powder (enzymatic purity: 93.5%) prepared in the same manner as in Example 1. To the obtained aqueous solution was added 5 mg. of crystalline NAD obtained in Example 1 as seeds for crystallization. The aqueous solution was then stirred at 5° C. for 6 hours, and the resulting crystals were separated and dried. The yield of crystalline NAD was 91.5 g., and the enzymatic purity was 99.8%.

EXAMPLE 4

The procedure of Example 3 was repeated except that there was employed a 50 w/v % aqueous solution of amorphous NAD obtained by dissolving in water 39 g. of amorphous NAD having an enzymatic purity of 92%, to give 35 g. of crystalline NAD. The thus obtained crystals contained 9.4% by weight of water and 90.5% by weight of NAD.

In 100 ml. of distilled water was dissolved 35 g. of the crystals at 46° C. Immediately after the dissolution, the aqueous solution was cooled to 20° C. The aqueous solution was then filtered through a membrane filter (commercially available under the commercial name "Millipore Filter" made by Millipore Corporation) having a pore size of 0.22 μm., and was lyophilized to give 32 g. of a high pure amorphous NAD. The thus obtained amorphous NAD powder contained 2.8% by weight of water and 97% by weight of NAD. The enzymatic purity of the powder was 99.8% on dry basis.

EXAMPLE 5

In 200 ml. of distilled water of 46° C. was dissolved 26 g. of the crystalline NAD obtained in Example 4, and immediately after the dissolution, the aqueous solution was cooled to 20° C. The aqueous solution was then filtered through a membrane filter having a pore size of 0.22 μm., and added to 1.8 liters of methanol with stirring. The resulting precipitate was collected by a decanter, washed with a slight amount of methanol and dried under reduced pressure to give 23 g. of high pure amorphous NAD. The thus obtained amorphous NAD powder contained 95.0% by weight of NAD and 3.0% by weight of water. The enzymatic purity of the powder was 97.9% on dry basis.

What we claim is:

1. A crystalline free acid type β-nicotinamide-adenine-dinucleotide tetrahydrate which is a triclinic system and has a space group of P$\bar{1}$ or P1 and lattice constants: a=8.861 Å, b=11.181 Å, c=8.630 Å, α=90.82°, β=103.40° and γ=109.71°.

2. A process for preparing crystalline free acid type β-nicotinamide-adenine-dinucleotide tetrahydrate in a triclinic system with a space group of P1 or P$\bar{1}$ and lattice constants: a=8.861 Å, b=11.181 Å, c=8.630 Å, α=90.82°, β=103.40° and γ=109.71°, which comprises cooling a 20 to 60 w/v% aqueous solution of amorphous β-nicotinamide-adenine-dinucleotide at a temperature of 0° to 20° C.

3. The process of claim 2, wherein said amorphous β-nicotinamide-adenine-dinucleotide has a purity of at least 90% by enzymatic analysis.

4. The process of claim 2, wherein said amorphous β-nicotinamide-adenine-dinucleotide is one purified by treatment with an acetate type high porous weakly basic anion exchange resin.

5. A process for preparing amorphous β-nicotinamide-adenine-dinucleotide which comprises dissolving crystalline free acid type β-nicotinamide-adenine-dinucleotide tetrahydrate in water, and recovering β-nicotinamide-adenine-dinucleotide in solid form by means of either freeze drying or preciptiation with an alcohol followed by separation and drying of the precipitate.

* * * * *

UNITED STATES PATENT AND TRADEMARK OFFICE
CERTIFICATE OF CORRECTION

PATENT NO. : 4,515,943
DATED : May 7, 1985
INVENTOR(S) : TOYOFUMI MIYA ET AL

It is certified that error appears in the above-identified patent and that said Letters Patent is hereby corrected as shown below:

On the cover page, Item [30], change "Oct. 12, 1980" to --- Oct. 15, 1980 ---.

Signed and Sealed this

Twenty-sixth Day of November 1985

[SEAL]

Attest:

DONALD J. QUIGG

Attesting Officer

Commissioner of Patents and Trademarks